United States Patent [19]
Chapman et al.

[11] Patent Number: 5,869,288
[45] Date of Patent: Feb. 9, 1999

[54] MOLECULAR CLONING OF COCKROACH ALLERGENS, AMINO ACID AND NUCLEOTIDE SEQUENCES THEREFORE AND RECOMBINANT EXPRESSION THEREOF

[75] Inventors: Martin Chapman; L. Karla Arruda, both of Charlottesville, Va.

[73] Assignee: The University of Virginia Patent Foundation, Charlottesville, Va.

[21] Appl. No.: 698,805

[22] Filed: Aug. 16, 1996

Related U.S. Application Data

[60] Provisional application No. 60/002,510 Aug. 18, 1995.
[51] Int. Cl.[6] .............................. C07H 21/04; C12N 1/21; C12N 15/00; C07K 14/435
[52] U.S. Cl. .................. 435/69.1; 435/252.3; 435/320.1; 530/300; 530/350; 536/23.5; 536/24.31
[58] Field of Search ........................ 435/6, 91.2, 7.1–7.9, 435/69.1, 252.3, 320.1; 530/388.1, 300, 350; 536/23.5, 24.31

[56] References Cited

PUBLICATIONS

Pollart et al. J. of Immunology 87: 511–521, 1991.
Chapman et al. J. Clinical Immunology 93: 205, 1994.
Arruda et al. International Archives of Allergy and Immunology 107: 295–297, 1995.

*Primary Examiner*—Carla J. Myers
*Attorney, Agent, or Firm*—Nixon & Vanderhye

[57] ABSTRACT

Four cockroach allergens are purified, described, characterized and sequenced. The nucleotide sequence responsible for expression of the allergen, and the amino acid sequence thereof, are set forth. These allergens induce IgE antibody binding, which may generate an allergic or asthmatic response in sensitive individuals. The allergens are expressed by one of the dominant cockroach strains in the United States, *B. germanica*. Sequence analysis allows classification of the allergens in major protein classifications.

17 Claims, 6 Drawing Sheets

Fig. 1

```
  1 AA ATG ATT GGC CTA AAG CTA GTG ACA GTT CTC TTT GCG GTT GCT    44
        M   I   G   L   K   L   V   T   V   L   F   A   V   A

45    ACC ATA ACA CAT GCA GCT GAG CTT CAA CGT GTT CCA TTG TAC    86
        T   I   T   H   A   A   E   L   Q   R   V   P   L   Y

87    AAA TTG GTG CAC GTT TTC ATT AAC ACT CAA TAC GCT GGT ATA   128
        K   L   V   H   V   F   I   N   T   Q   Y   A   G   I

129    ACC AAG ATT GGA AAC CAG AAC TTC CTA ACA GTA TTC GAT AGC   170
        T   K   I   G   N   Q   N   F   L   T   V   F   D   S

171    ACC TCA TGC AAT GTA GTC GTT GCC AGT CAA GAA TGC GTT GGT   212
        T   S   C   N   V   V   V   A   S   Q   E   C   V   G

213    GGA GCT TGT GTA TGT CCA AAT CTA CAA AAA TAT GAG AAA CTT   254
        G   A   C   V   C   P   N   L   Q   K   Y   E   K   L

255    AAA CCG AAG TAT ATC TCT GAT GGG AAT GTA CAG GTG AAA TTC   296
        K   P   K   Y   I   S   D   G   N   V   Q   V   K   F

297    TTC GAC ACT GGT AGC GCA GTT GGT AGA GGC ATT GAA GAT TCC   338
        F   D   T   G   S   A   V   G   R   G   I   E   D   S

339    CTT ACG ATT TCT AAC CTC ACG ACA TCT CAA CAA GAC ATT GTC   380
        L   T   I   S   N   L   T   T   S   Q   Q   D   I   V

381    CTT GCC GAT GAA CTC AGT CAA GAA GTC TGC ATT CTA TCT GCT   422
        L   A   D   E   L   S   Q   E   V   C   I   L   S   A

423    GAC GTA GTT GTA GGA ATA GCA GCC CCA GGA TGC CCT AAT GCA   464
        D   V   V   V   G   I   A   A   P   G   C   P   N   A

465    CTG AAA GGA AAA ACT GTT CTC GAA AAC TTT GTC GAA GAA AAT   506
        L   K   G   K   T   V   L   E   N   F   V   E   E   N

507    CTT ATT GCG CCT GTC TTT TCT ATT CAT CAT GCT AGA TTT CAA   548
        L   I   A   P   V   F   S   I   H   H   A   R   F   Q

549    GAT GGA GAA CAT TTC GGA GAA ATT ATT TTC GGA GGT TCT GAT   590
        D   G   E   H   F   G   E   I   I   F   G   G   S   D
```

Fig. 1A

```
591   TGG AAA TAC GTT GAT GGT GAA TTC ACT TAT GTT CCA CTT GTG    632
       W   K   Y   V   D   G   E   F   T   Y   V   P   L   V

633   GGT GAT GAT TCC TGG AAG TTC AGG CTG GAT GGT GTG AAA ATA    674
       G   D   D   S   W   K   F   R   L   D   G   V   K   I

675   GGT GAC ACA ACT GTT GCT CCA GCA GGT ACA CAG GCC ATC ATC    716
       G   D   T   T   V   A   P   A   G   T   Q   A   I   I

717   GAC ACA AGC AAA GCT ATC ATT GTC GGA CCT AAA GCC TAT GTT    758
       D   T   S   K   A   I   I   V   G   P   K   A   Y   V

759   AAT CCA ATC AAC GAA GCT ATT GGG TGT GTA GTG GAA AAG ACA    800
       N   P   I   N   E   A   I   G   C   V   V   E   K   T

801   ACA ACC AGG AGA ATA TGC AAG CTT GAC TGC AGC AAG ATA CCA    842
       T   T   R   R   I   C   K   L   D   C   S   K   I   P

843   TCT CTC CCT GAT GTC ACA TTT GTG ATC AAT GGC AGG AAT TTC    884
       S   L   P   D   V   T   F   V   I   N   G   R   N   F

885   AAC ATC AGC TCA CAA TAT TAC ATC CAA CAG AAC GGG AAC TTG    926
       N   I   S   S   Q   Y   Y   I   Q   Q   N   G   N   L

927   TGC TAT TCC GGC TTC CAA CCA TGC GGT CAC TCC GAT CAC TTT    968
       C   Y   S   G   F   Q   P   C   G   H   S   D   H   F

969   TTT ATT GGT GAC TTC TTT GTT GAT CAT TAT TAT TCT GAA TTC    1010
       F   I   G   D   F   F   V   D   H   Y   Y   S   E   F

1011  AAC TGG GAG AAC AAG ACC ATG GGA TTC GGC CGT TCA GTA GAA    1052
       N   W   E   N   K   T   M   G   F   G   R   S   V   E

1053  AGC GTC TAA GAA TTT CAA CAT CAA GAT GGA CTT CAG AGA TTA    1094
       S   V   ***

1095  CTT CGG AAT CAC TAA TAA GAC ATT CAC GAG ACT TAC GAA GAC    1136
1137  CAC TAC AGT TTT GGA TAT GAA TGA TGA CAA ATA ACT GAA GAC    1178
1179  TTT TCA TTA TAT GAC ATG GAG AAG ATT TTT TTA AAG TCG CCT    1220
1221  ATT ATT ACT TTT TTC GCA CAC TTT TAT GTA TAC AGC TAC TGA    1262
1263  TGT CTT AAA ATA AAC TGG AAA TAT TTT GAA TTT TCT A19       1318
```

Fig. 2

```
  1: C GCA GTT TTG GCA CTA TGT GCA ACA GAT ACA TTG GCG AAC GAA
       A   V   L   A   L   C   A   T   D   T   L   A   N   E

44:   GAT TGT TTT AGA CAT GAA TCA TTG GTT CCA AAC CTT GAT TAT
       D   C   F   R   H   E   S   L   V   P   N   L   D   Y

86:   GAA AGG TTC AGA GGT TCG TGG ATT ATT GCA GCC GGC ACT TCC
       E   R   F   R   G   S   W   I   I   A   A   G   T   S

128:   GAA GCG CTC ACC CAA TAC AAA TGC TGG ATC GAC AGG TTT TCA
       E   A   L   T   Q   Y   K   C   W   I   D   R   F   S

170:   TAT GAC GAT GCG TTG GTT TCT AAG TAT ACT GAT TCA CAA GGA
       Y   D   D   A   L   V   S   K   Y   T   D   S   Q   G

212:   AAG AAT AGG ACT ACT ATC AGA GGA CGA ACT AAA TTT GAA GGC
       K   N   R   T   T   I   R   G   R   T   K   F   E   G

254:   AAC AAG TTT ACT ATC GAT TAT AAT GAT AAA GGG AAA GCA TTT
       N   K   F   T   I   D   Y   N   D   K   G   K   A   F

296:   TCT GCG CCA TAC TCT GTT CTA GCA ACT GAT TAC GAA AAT TAC
       S   A   P   Y   S   V   L   A   T   D   Y   E   N   Y

338:   GCA ATT GTG GAA GGC TGT CCC GCT GCA GCT AAT GGA CAT GTA
       A   I   V   E   G   C   P   A   A   A   N   G   H   V

380:   ATT TAT GTT CAA ATC CGA TTT TCG GTG AGG AGA TTT CAC CCC
       I   Y   V   Q   I   R   F   S   V   R   R   F   H   P

422:   AAG CTG GGT GAT AAA GAA ATG ATA CAG CAC TAC ACT TTG GAT
       K   L   G   D   K   E   M   I   Q   H   Y   T   L   D

464:   CAG GTG AAT CAA CAC AAG AAG GCT ATA GAA GAA GAC TTA AAG
       Q   V   N   Q   H   K   K   A   I   E   E   D   L   K

506:   CAC TTC AAT TTG AAG TAC GAG GAC TTA CAC TCC ACA TGT CAC
       H   F   N   L   K   Y   E   D   L   H   S   T   C   H

548:   TAA GTATGAAATGTTCATATTTATTGTAGGAAAATAAAACCTTCTAATGAATTA29
       ***
```

Fig. 3

```
  1 CT TAT AAA CTG ACA TAC TGT CCC GTG AAG GCT CTG GGA GAG CCA   44
        Y   K   L   T   Y   C   P   V   K   A   L   G   E   P

45    ATT CGC TTC CTT CTG TCT TAT GGA GAG AAA GAT TTT GAA GAT   86
        I   R   F   L   L   S   Y   G   E   K   D   F   E   D

87    TAT CGT TTC CAG GAG GGA GAT TGG CCT AAT TTG AAA CCT TCC  128
        Y   R   F   Q   E   G   D   W   P   N   L   K   P   S

129    ATG CCA TTT GGT AAA ACA CCA GTG TTG GAG ATT GAT GGG AAG  170
        M   P   F   G   K   T   P   V   L   E   I   D   G   K

171    CAA ACA CAC CAG TCT GTT GCC ATT TCT CGC TAT CTT GGT AAG  212
        Q   T   H   Q   S   V   A   I   S   R   Y   L   G   K

213    CAG TTT GGC CTC AGT GGT AAG GAT GAT TGG GAG AAC TTG GAG  254
        Q   F   G   L   S   G   K   D   D   W   E   N   L   E

255    ATC GAC ATG ATC GTC GAC ACC ATC TCT GAC TTC AGG GCT GCC  296
        I   D   M   I   V   D   T   I   S   D   F   R   A   A

297    ATT GCT AAT TAC CAT TAT GAT GCT GAT GAA AAT TCA AAG CAG  338
        I   A   N   Y   H   Y   D   A   D   E   N   S   K   Q

339    AAG AAA TGG GAC CCT CTC AAG AAG GAA ACC ATT CCT TAC TAC  380
        K   K   W   D   P   L   K   K   E   T   I   P   Y   Y

381    ACC AAA AAG TTT GAT GAA GTG GTG AAG GCT AAC GGA GGA TAC  422
        T   K   K   F   D   E   V   V   K   A   N   G   G   Y

423    CTT GCT GCT GGA AAG CTG ACA TGG GCA GAC TTC TAC TTC GTT  464
        L   A   A   G   K   L   T   W   A   D   F   Y   F   V

465    GCC ATT CTC GAC TAT TTG AAT CAC ATG GCT AAA GAA GAC CTG  506
        A   I   L   D   Y   L   N   H   M   A   K   E   D   L

507    GTG GCC AAT CAA CCC AAT TTG AAG GCT TTG CGG GAG AAA GTA  548
        V   A   N   Q   P   N   L   K   A   L   R   E   K   V

549    TTG GGT TTG CCT GCT ATC AAA GCA TGG GTC GCC AAG CGT CCT  590
        L   G   L   P   A   I   K   A   W   V   A   K   R   P

591    CCT ACA GAT CTG TAA GAA AAA TGT GCC ATG GCA AAA AAA TTC  632
        P   T   D   L   ***
```

Fig. 3A

```
633    ATG TTG CAT GTA ACA CTG AGA TCA TAA CGA TGT TCT AAA AGA    674
675    AAT TTT GTT ACG CAT AAT GAT TTT ATG AAA GTA TTT TGT TAG    716
717    CAG CTT TGC TCT ATA ATA ATC ACT AGA CCA TAT TTA AAA GGC    758
759    AAA AAC GAA CAT TTT CTT CAT AAA AGG CAA AAA TAG CCA AAA    800
801    AAT ACT TTT GTA TTA AAA TAT TCA TTG ACG CTG ATT CTT ACA    842
843    TTT AAT TCT TCA CAA TTT AAG AAT TTT TTA ACA ATA GTA ATT    884
885    ACG ATC AAC ATT TCA GAT CTG TTT AGA TAT GAT TGC AAA GCT    926
927    TGT TTA TAA TCA GAA AAT GAC TTC CTA AAA TCA ACA GCA TAT    968
969    GGC GCA AAA TTT TTC GTT CTA AAT TTC AGT TTT TTT AAA TGT   1010
1011   ATA ATT TTT TTG GTA AAC TTT TAT TTA CTA GAA ATT TGA TCC   1052
1053   AGA AGT AGA CTG ATA ATT TCC TTT ACT TAC TTT TTG GTA TTA   1094
1095   AAC AAA GTT GGA AAC AAA ATA ATT TTG A$_{19}$              1140
```

Fig. 4

```
  1  GA GAG GTA CCA CAA GCC ACC ACC AAC AAC ACC GTC GCC ATG GAT   44
         E   V   P   Q   A   T   T   N   N   T   V   A   M   D

45     GAA ATT CCA GCA GAA CAG GTC GTA CTG TTG AAG AAG GCT TTC   86
         E   I   P   A   E   Q   V   V   L   L   K   K   A   F

87     GAT GCC TTC GAT CGT GAG AAG AAG GGT TGC ATC TCC ACT GAG  128
         D   A   F   D   R   E   K   K   G   C   I   S   T   E

129     ATG GTA GGC ACC ATC CTG GAG ATG TTG GGT ACC CGT CTG GAC  170
         M   V   G   T   I   L   E   M   L   G   T   R   L   D

171     CAG GAC ATG CTG GAT GAG ATC ATC GCT GAA GTC GAC GCT GAC  212
         Q   D   M   L   D   E   I   I   A   E   V   D   A   D

213     GGT TCC GGT GAG CTG GAG TTC GAG GAA TTC TGT ACA TTG GCC  254
         G   S   G   E   L   E   F   E   E   F   C   T   L   A

255     TCT AGG TTC CTG GTT GAA GAG GAT CGT GAA GCC ATG CAG CAC  296
         S   R   F   L   V   E   E   D   R   E   A   M   Q   H

297     GAA CTC CGA GAA GCT TTC AGA TTA TAC GAC AAG GAA GGC AAC  338
         E   L   R   E   A   F   R   L   Y   D   K   E   G   N

339     GGC TAC ATC ACA ACA GCT GTC CTA CGC GAG ATC CTG AAG GAG  380
         G   Y   I   T   T   A   V   L   R   E   I   L   K   E

381     CTC GAT GAC AAA ATA ACC GCT GAG GAC TTG GAT ATG ATG ATT  422
         L   D   D   K   I   T   A   E   D   L   D   M   M   I

423     GAG GAA ATT GAC TCT GAC GGT TCC GGA ACC GTT GAC TTT GAT  464
         E   E   I   D   S   D   G   S   G   T   V   D   F   D

465     GAA TTC ATG GAA GTC ATG ACT GGA GAA TAA ATG CCA TTT TAT  506
         E   F   M   E   V   M   T   G   E   ***

507     GCT TCA AAA CTT AAG TCA TCT TTC TTC AAT GGA CTG CCT CCG  548
549     AGC TAT CTG AGC TTT AGG AAT GAG TTC ATC CAA AAG ACA ATC  590
591     TTG TAT TCT TAT AAT CGT ATG GCA ATG TAA ATT ATC ATT CAA  632
633     CAT CAT TTT GAT AAA TTG TTA CTA AAT TTT ATG TTT CTG TAC  674
675     ATA TCA AAT TTT ATT ATG AAA TTT ATT GGG GCC TGC CTA TAA  716
717     ACA AGA CAA TGT GTA TAT GTT TAC TTT AAC ACC AGT ATT ATT  758
759     ATA CAA TAA TGT GAA ATA AAA GAC TTC AGA ACT TTG TAT GA₃₈  836
```

MOLECULAR CLONING OF COCKROACH ALLERGENS, AMINO ACID AND NUCLEOTIDE SEQUENCES THEREFORE AND RECOMBINANT EXPRESSION THEREOF

This application claims priority of provisional application Serial No. 60/002,510, filed Aug. 18, 1995.

BACKGROUND OF THE INVENTION

1. Field of the Invention

This invention pertains to the isolation, purification and characterization of four separate cockroach allergens identified as binding to IgE antibodies in humans, and thereby inducing, in sensitive individuals, an allergic or asthmatic response. Specifically, four cockroach allergens, designated according to the WHO allergens nomenclature as Bla g 2, Bla g 4, Bla g 5, and Bla g 6 are identified, Bla 4, 5 and 6 having never before been purified. Additionally, the nucleotide sequences for the genes responsible for expression of these allergens are given, and the amino acids sequences therefore. Recombinant expression of the allergens is achieved, leading to modification of the same.

2. Background of the Prior Art.

It has been known since at least 1964 that cockroaches (CR) produce potent allergens that can cause asthma and allergic respiratory disease. Numerous attempts over the past twenty years have been made to identify the important CR allergens that cause allergic (IgE) antibody responses in CR sensitive patients. CR extracts used for allergy testing comprise aqueous extracts of ground CR bodies. These extracts contain many other CR proteins in addition to the relevant allergens. The approach adopted by many research groups has been to use biochemical separation and purification techniques to isolate the allergens and to assess their allergenic importance by reactivity, in vitro and in vivo, with IgE antibody. Using this approach, some allergens have been characterized according to their molecule size and charge, and reactivity with IgE. Two of these were sufficiently well characterized to be included in the WHO allergens nomenclature, Bla g 1 and Bla g 2.

Notwithstanding these advances, the actual protein structures of the allergens were not known. Further, only the two allergens had been purified. It was not, therefore, possible to define the chemical structures of these allergens. This precludes developing information to determine antigenic sites in the molecules (IgE binding epitopes), or other information involved in the immune response. Additionally, isolation of the nucleotide sequence is a pre-requisite to its recombinant expression, and modification, through fusion technology, site-specific and site-directed mutation, and the like, so as to develop methods of treating and diagnosing CR allergies. The same has been successfully done in analagous areas, such as in connection with the house dust mite allergen Der P 2.

Isolation, characterization, and recombinant expression of the CR allergens can be used to improve methods of diagnosing CR allergy, which are currently confined to generic extract scratch testing, which precludes identifying the specific allergen responsible; developing new treatments for CR allergies and developing methods for controlling CR infestation.

Accordingly, it remains an object of those of ordinary skill in the art to purify, characterize, sequence and recombinantly express CR allergens.

SUMMARY OF THE INVENTION

The above objects, and others elaborated on through the disclosure below, have been achieved through a new strategy that allowed determination of the primary amino acid sequence of four German cockroach (*B germanica*) allergens. Nucleotide cDNA sequence information and purification has similarly been achieved.

Molecular cloning techniques were used to isolate cDNA clones encoding CR allergens, and to determine the nucleotide sequence of those clones. The amino acid sequence is deduced from the nucleotide sequence to obtain the complete chemical structure of the protein. The process involves isolating mRNA from CR and constructing a cDNA library in bacteria. The library was screened using IgE antibodies from CR allergic patients and six clones which reacted with the IgE antibody serum pool were identified. Based on the prevalence and strength of reactivity, three clones were selected for nucleotide sequencing and their deduced amino acid sequence was determined. These clones were subsequently designated Bla g 4, Bla g 5 and Bla g 6. They cause IgE antibody responses in 40–60% of CR allergic patients. A further cDNA clone encoding previously characterized, but unsequenced Bla g 2 was isolated using mouse antibodies to the protein. In addition, the Bla g 2 protein (isolated by immunochemical methods) was sequenced by conventional amino acid sequencing techniques.

Comparing the sequences obtained with other sequences in protein data bases, it has been established that the four allergens characterized belong to certain protein families. Bla g 2 is indicated to be an aspartic protease. Bla g 4 belongs to the family of calycin proteins, which unexpectedly allowed the identification of other allergens. Bla g 5 shows substantial homology with glutathione transferase and Bla g 6 is a troponin. This information may allow the development of methods to interfere with the biologic functions of the proteins as a method of CR control, that is, by interfering with the enzymatic activity, e.g., of 2 and 5.

The information obtained also permits the structural modification of the molecules, and alteration of specific amino acid residues in proteins, to identify specific amino acid residues recognized by IgE antibodies. The sequence information also allows the practitioner to design short peptides which can be chemically synthesized and tested for their ability to induce T-cell response in allergic patients. These responses control IgE antibody production, and the identification of appropriate peptides is a key step in developing a vaccine. Similarly, modalities for addressing reactivity by alternating the three-dimensional structure of each allergen, and recombinant expression for use in allergy diagnosis and in treatment, is made possible by this information.

DETAILED DESCRIPTION OF THE DRAWINGS

FIG. 1 gives the nucleotide and deduced amino acid sequence of CR allergen Bla g 2 (SEQ ID NO: 1,2).

FIG. 2 gives the nucleotide and deduced amino acid sequence of CR allergen Bla g 4 (SEQ ID NO: 3,4).

FIG. 3 gives the nucleotide and deduced amino acid sequence of CR allergen Bla g 5 (SEQ ID NO: 5,6).

FIG. 4 gives the nucleotide and deduced amino acid sequence of CR allergen Bla g 6 (SEQ ID NO: 7,8).

DETAILED DESCRIPTION OF THE INVENTION

The nucleotide sequence for the gene responsible for expression of each of the four CR allergens discussed herein, and the corresponding amino acid sequence, is determined and disclosed below. Additionally, recombinant expression of the allergens, as exemplified by the use of Bla g 4, is also set forth. It should be noted the techniques for isolation, per se, although fully disclosed, do not constitute part of the invention. Similarly, recombinant expression, as described, can be similarly achieved for each of the allergens, and employs recombinant techniques familiar to those of skill in the art. Following the discussion of purification, isolation and characterization of each of the allergens, presented below is an analysis of the protein families in which each allergen can be characterized. The identity of the family, and therefore the biological activity of the allergen, may be a key to both inhibiting allergenic response, and CR infestation.

EXPERIMENTAL PROCEDURES

Bla g 2

Purification of CR Allergens

*B. germanica* frass (feces, secretions, egg cases and body parts) was extracted in borate-buffered saline, pH 8.0 (BBS), overnight at 4° C. After centrifugation at 18,000 rpm, the supernatant was dialyzed against $BBS_L$ and ether extracted. Bla g 2 was purified by affinity chromatography over mAb 8 F4 immunosorbent Pollart et al., J. Allergy Clin. Immunol., 87, 511–521 (1991); followed by elution from a C18 reverse phase HPLC column (Brownlee Labs, Santa Clara, Calif.) using a 0–80% gradient of acetonitrile in 0.1% trifluoroacetic acid. Alternatively, mAb affinity purified Bla g 2 was further purified by electroelution from SDS-PAGE gels using a micro-electroelutor (Centrilutor, Amicon, Beverly, Mass.) according to the method of LeGendre and Matsudaira, A Practical Guide, Academic Press, 49–69 (1989). Fifty $\mu$g affinity purified allergen were applied to 8 lanes of a 12% SDS-PAGE gel and the 36 kDa bands were excised, electroeluted for 2 hours, and concentrated by centrifugation. Purity was assessed by SDS-PAGE using either an 8–25% silver-stained gel on a PhastSystem (Pharmacia Piscataway, N.J.) or a Coomassie Blue stained 12% gel.

Amino Acid Sequencing

Amino terminal amino acid sequences of HPLC purified allergens were determined by Edman degradation using a gas phase sequencer (Applied Biosystems, Model 470-A, Foster City, Calif.). Seven tryptic peptides (7–22 residues) of electroeluted Bla g 2, comprising 84 amino acid residues, were sequenced. Affinity purified Bla g 2 was also separated on a 12% SDS-PAGE gel and transferred to polyvinylidene difluoride (PVDF) membrane (Immobilon-P, Millipore, Bedford, Mass.). The $NH_2$-terminal amino acid residues of the 36 kDa and 70 kDa bands were sequenced off the membrane (14 and 10 residues, respectively).

Molecular Cloning and Secuencing of Bla a 2 cDNA

Total RNA was extracted from adult *B. germanica* or *P. americana* of mixed sexes, with 5M guanidinium thiocyanate using the method of Chirgwin et al., Biochemistry, 18, 5294–5299 (1979). Messenger RNA was obtained using a FastTrack kit (Invitrogen, San Diego, Calif.). A *B. germanica* cDNA library was prepared from 10 $\mu$g mRNA in the Uni-ZAP-XR expression vector (Stratagene, La Jolla, Calif.). The library was screened using polyclonal mouse anti-Bla g 2 antiserum, with an IgG ab titer>100,000 as determined by ELISA. Recombinant plaques were grown on NZY agar and protein expression was induced using nitrocellulose filters soaked in 10 MM IPTG. Filters were incubated in blocking solution (10% dried mil, 0.2% bovine serum albumin, 0.4% goat serum, 0.03% gelatin), followed by a 1:5,000 dilution mouse anti-Bla g 2 antiserum, preabsorbed with *E. coli* lysate. Positive plaques were identified using 1:2,000 dilution alkaline phosphatase labeled anti mouse IgG and BCIP/NBT substrate (KPL, Gaithersburg, Md.). A single positive plaque, containing a 1,318 bp cDNA insert coding for Bla g 2, was isolated after screening 296,000 pfu of *B. germanica* cDNA library. Both strands of the Bla g 2 cDNA were sequenced by dideoxynucleotide chain termination using Sequences (United States Biochemical, Cleveland, Ohio).

Sequence Analysis

Protein or peptide sequences were compared with the National Biomedical Research Foundation, Swiss-Prot and GenBank data bases using FASTA and sequence alignments were carried out using the gcg program Pearson et al., Proc. Nat'l. Acad. Sci. USA 85, 2444–2448 (1988).

IgE Antibodies and Immediate Hypersensitivity Skin Testing

Sera were obtained from 93 CR allergic patients who had either been recruited from the University of Virginia Allergy Clinics or who had previously presented to hospital Emergency Rooms with asthma. A further 13 sera were collected from CR allergic patients living in New York or Puerto Rico. All patients had asthma and the majority were adults (>16 years old). Eight patients were children (aged 4–10). All patients had serum IgE ab to CR allergens detectable by radioallergosorbent test (RAST) (CR RAST>40 units/ml, 1 unit=~0.1 ng IgE). Sera from 19 non-allergic individuals were used as controls.

Quantitative intradermal skin tests were carried out using serial 10-fold dilutions of *B. germanica* extract (1/20 w/v, Allergy Laboratories of Ohio, Columbus, Ohio), or purified Bla g 2, from $10-10^{-6}$ $\mu$g/ml, as previously described, Pollart et al., Supra. Skin testing, and collection of sera for use in these studies, was approved by the Human Investigation Committee of the University of Virginia.

Immunoassays for IaE Antibodies to CR Allergens

Serum IgE ab Bla g 2 were measured using a mAb based solid-phase RIA. Briefly, 1 $\mu$g mAb 8F4 (anti-Bla g 2) was coated onto plastic microtiter wells, followed by successive incubations with 0.5 $\mu$G *B. germanica* frass extract and human sera, diluted 1:2 and 1:10. Bound IgE ab were detected using 2 ng $^{125}$I-labeled anti human IgE. The assays were quantitated using sera from two CR allergic patients (B. A and M. A.) with high levels of IgE ab to Bla g 1 or Bla g 2, respectively, to construct control curves. Each serum was arbitrarily assigned a value of 1,000 units/ml of IgE ab.

Inhibition RIA for Comparing Bla g 2 Antigen Expression in CR Species

Twenty $\mu$g electroeluted Bla g 2 were radiolabeled with 1 mCi $^{125}$I using the Chloramine T technique (specific activity 18.5 $\mu$Ci/$\mu$g) Chapman et al., J. Immunol. 125, 587–592 (1980). Serial doubling dilutions of Bla g 2, *B. germanica* frass extract or *B. germanica* commercial extract (Greer Laboratories, Lenoir, N.C.) were used to inhibit the binding of $^{125}$I-Bla g 2 to mouse IgG anti-Bla g 2 ab. Allergens were incubated for 2 hours with 0.1 ml 1:4,000 dilution of mouse anti-Bla g 2 antiserum, followed by 3 ng $^{125}$I-Bla g 2 for 2 hours, and precipitated overnight at 4° C. with 1:15 dilution goat anti-mouse IgG (Chemicon, El Segundo, Calif.). Precipitates were washed with BBS and counted in a gamma-counter. Expression of Bla g 2 was compared in *P. americana* extracts. Whole body extract was prepared by homogenizing 133 g CR with BBS in a blender, extracting at 1:5 w/v overnight at 4° C., and decanting the supernatant after centrifugation (6,000 rpm×30 min). Frass extract was prepared as for *B. germanica*. Commercial *P. americana* extracts (n=11) were obtained from ten U.S. allergen manufacturers: Allergy Laboratories of Oklahoma (Oklahoma City, Okla.), Allergy Laboratories of Ohio (Columbus, Ohio), Center Laboratories (Port Washington, N.Y.), Greer Laboratories (Lenoir, N.C.), Miles Laboratories (Elkhart, Ind.), Antigen Labs (Liberty, Mo.), Nelco (Deer Park, N.Y.), ALK/Berkeley (Milford, Colo.), Bencard (Bencard, Miss), Meridian (Round Rock, Tex.), Iatric (Tempe, Ariz.).

Northern Analysis of the Expression of Bla g 2 mRNA

For Northern blots, B. germanica and P. americana mRNA was isolated from total RNA using the Poly A Tract mRNA isolation system (Promege, Madison, Wis.). Samples containing 0.5–6 µg mRNA were electrophoresed in formaldehyde denaturing 1% agarose gels, followed by transfer to a Zetabind nylon membrane (Cuno, Meridien, Conn.). A 1.3 kb Sma I/Kpn I restriction fragment from a pBLUESCRIPT phagemid DNA comprising the complete Bla g 2 cDNA, and an 8.6 kb Bam HI fragment containing Neurospora crassa ribosomal DNA (pRW528) were labeled with [$\alpha$-$^{32}$P] dCTP by random priming and used to probe the blots. Hybridization was carried out at 37° C., as previously described, Arruda et al., J. Immunol. 149, 3354–3359 (1992).

Bla g 2 Measurements in CR Tissues and Secretions

To prepare tissue extracts, CR were dissected and body parts identified according to the method of Bell, The Laboratory Cockroach, Chapman & Hall (1951). Tissues were homogenized with a polytron and extracted overnight in 0.5 ml BBS at 4° C. After centrifugation at 12,000 rpm for 15 minutes, extracts were stored at −20° C. until assayed. CR washes were obtained by placing 3–15 adult CR of mixed sexes in a glass breaker containing 10 ml 5 mM ammonium bicarbonate. After 4–6 hours, CR were removed and the walls of the beaker were rinsed with the ammonium bicarbonate buffer. The solution was centrifuged at 12,000 rpm for 15 minutes, freeze-dried, weighted, reconstituted in 0.25 ml BBS and stored at −20° C. Bla g 2 levels in CR tissues and washes were measured by mAb ELISA.

RESULTS

Allercenic Importance of Bla g 2

Sera from 106 CR allergic patients with asthma living in different geographic areas in the United States were analyzed for IgE ab BLA g 2 by mAb based RIA. The results showed that 57.6% of these patients had detectable IgE ab Bla g 2. The prevalence of IgE ab to Bla g 2 was higher among patients with IgE ab to CR of>200 RAST units/ml (70%, n=58), as compared to the group with<200 RAST units/ml (42%, n=48). The biologic activity of purified Bla g 2 was assessed by quantitative intradermal skin testing of seven selected CR allergic patients. These patients gave positive immediate skin reactions (>8×8 mm wheal) to allergen concentrations down to $10^{-3.5}$ µg/ml, whereas non-allergic controls showed no reaction to concentrations up to 10 µg/ml (and had no detectable serum IgE ab). Skin test reactivity correlated with serum IgE ab Bla g 2 and distinct patterns of reactivity to the allergens were observed.

Complete Nucleotide and Amino Acid Sequence of Bla g 2

We focused on sequencing Bla g 2, because of its allergenic importance and because this protein has been used extensively as a market of environmental CR allergen exposure, Call et al., J. Pediatrics 121, 862–866 (1992). The Bla g 2 sequence was determined using a combination of protein sequencing and cDNA cloning. Previous studies showed that single step mAb affinity chromatography yielded 36 kDa Bla g 2, as well as additional bands, MW 20 kDa and 70 kDa, which co-purified with the allergen, Pollart, supra. For amino acid sequencing, Bla g 2 was further purified by reverse-phase HPLC or electroelution from SDS-PAGE gels. Three protein peaks were obtained on reverse phase HPLC, which separated Bla g 2 from the 20 kDa contaminant. The NH$_2$-terminal amino acid sequence of Bla g 2 (35 residues) was determined from HPLC peak 2. This sequence was subsequently confirmed by sequencing Bla g 2 (14 residues) which had been electroeluted onto PVDF membrane. The NH$_2$-terminal sequence of the 20 kDa protein did not share significant homology to Bla g 2 or other proteins, suggesting that it was not a breakdown product of Bla g 2 (data not shown). Tryptic peptides were prepared from electroeluted Bla g 2 and internal peptide sequences (comprising 84 residues) were obtained which, together with the NH$_2$-terminal sequence, comprised 36.3% of the entire molecule. In addition, the first 10 residues of the 70 kDa protein sequenced off PVDF membrane were identical to the NH$_2$-terminal sequence of Bla g 2, suggesting that the 70 KDa was a dimer of Bla g 2.

Although ~60% of CR allergic patients had IgE ab to Bla g 2, attempts to screen the B. germanica cDNA library with pooled IgE ab, to identify a Bla g 2 cDNA clone, were unsuccessful. The cDNA coding for Bla g 2 was identified using mouse polyclonal IgG anti Bla g 2 ab. The full length cDNA contained an open reading frame of 1,056 nucleotides, encoding a 24 amino acid putative signal peptide and a 328 amino acid protein, with a predicted molecular weight of 35,939 Da (FIG. 1). Inspection of the nucleotide sequence identified a polyadenylation signal 22 nucleotides upstream from the poly(A) tail and three potential N-linked glycosylation sites. However, the close agreement between the molecular mass obtain by sequencing and by SDS-PAGE analysis suggests that the allergen is not glycosylated. The deduced amino acid sequence of Bla g 2 showed 91% identity to the amino acid sequences determined by Edman degradation from Bla g 2 protein.

The sequence information set forth above pertains to Bla g 2, a previously identified (but not characterized) CR allergen. Through similar methods, three previously unidentified allergens, Bla g 4, 5 and 6 have been identified and are discussed below. It is important to note that prior to this invention, these allergens were not known nor indicated to be present in CR extracts, and these allergens had not been purified, nor were means available to purify them.

RESULTS

Molecular Cloning of Blattella germanica Allergens For Allergens Bla g 4, Bla g 5 and Bla g 6

A unidirectional B. germanica cDNA library was screened using pooled IgE antibodies from CR allergic patients with asthma. Six positive plaques were cloned and re-screened against a panel of sera from CR allergic patients by plaque immunoassay. Most patients had IgE antibody to two or more clones (e.g. SW, bg7, bg12A; RM bg7, bg12A, bg14) and showed different patterns of IgE antibody binding, suggesting that B. germanica produced multiple allergens. The strongest intensity of IgE antibody binding was observed using protein encoded by clone bgl2A and—60% ($^{47}/_{73}$) of sera from CR allergic patients gave positive IgE antibody plaques to this protein. Nucleotide sequencing showed that bg12A cDNA contained a 546 bp open reading frame, coding for a 182 amino acid protein with an estimated molecular weight of 20,904 daltons (FIG. 2). The allergen encoded by clone bg12 A was provisionally designated Blattella germanica allergen 4, Bla g 4, in keeping with the revised WHO/IUIS allergen nomenclature. The allergen encoded by clone 16 was designated Bla g 5 and the allergen encoded by clone by 12B was designated Bla g 6, similarly.

Expression of Recombinant Bla g 4 in E. Coli

Bla g 4 plasmid DNA (50 ng) was used as template to generate a 546 PCR product containing BamH I and Xho I restriction enzyme sites, to allow undirectional subcloning into the pGEX-4TI expression vector (Pharmacia Biotech, Piscataway, N.J.). Primers for PCR were synthesized as follows: 5' CGC GGA TCC ACA GAT ACA TTG GCG AA 3' (sense) and 5' CCG CTC GAG TTA GTG ACA TGT GGA GTG 3' (antisense). PCR incubations were 1 minute at 94° C.; 1 minute at 37° C. or 42° C.; and 3 minutes at 72° C., for 30 cycles in a 50 $\mu$l volume. An initial 5 minute incubation step at 95° C. was performed and each reaction was terminated for 15 minutes at 72° C. The 546 bp PCT amplified DNA was ligated into BamH I/Xho I digested pGEX-4t1. DNA ligation and transformation of competent E. coli strain TOP10F was achieved (Invitrogen, San Diego, Calif.). Expression of Bla g 4 as a fusion protein with glutathione-S-transferase (GST) was induced with 1 mM IPTG, and recombinant protein was purified from cell lysates by chromatography over glutathione agarose. Digestion with thrombin (10 units/mg protein, for 18 h at room temperature) released the 21 kd Bla g 4 protein, which was recovered in the flow-through following further purification over glutathione agarose. To assess purity, rBla g4 was analyzed by silver-stained SDS-PAGE and by size exclusion HPLC, over a Superdex 75 HR 10/20 column(Pharmacia). Recombinant Bla g 4 eluted as a single HPLC peak, and the amino acid sequence of the 5 NH$_2$-terminal residues was confirmed by Edman degradation. The final yield was 250 $\mu$g purified rBla g 4 per liter of culture.

Immunoassay for IgE Antibodies to Recombinant Bla g 4 (rBla g4)

IgE anti-Bla g 4 ab were measured in sera from 73 CR allergic asthmatic patients, using an antigen-binding RIA. Briefly, 9 $\mu$g rBla g4 was radiolabeled with 0.5 mCi $^{125}$I, using the Chloramine-T technique (specific activity 3 $\mu$Ci/$\mu$g). Serum dilutions of 1:2 and 1:10 were incubated with $^{125}$I-rBla g 4 (~100,000 cpm added) for 4 hours at room temperature, and precipitated overnight at 4° C. with 50 $\mu$l sheep anti-human IgE (The Binding Site, San Diego, Calif.). IgE myeloma serum (P.S.) diluted 1:200 was used as carrier. Precipitates were washed with BBS and counted in a gamma-counter. The assay was quantitated using a control curve, constructed with patient S. W. serum, assigned to contain 10,000 units/ml IgE antibody.

Demonstration of IgE Antibody Responses to Recombinant Bla g 4 (rBla g 4).

PCR amplified DNA encoding Bla g 4 was ligated into pGEX-4T1 and expressed as a GST fusion protein in E. coli. Recombinant Bla g 4 was obtained from bacterial lysates by glutathione affinity chromatography and thrombin cleavage, and the pure protein migrated as a single band of 18 kd on an 8–24% gradient SDS-PAGE. Serum IgE ab to rBla g 4 was compared in 73 sera from CR allergic patients by antigen binding RIA. The prevalence of IgE ab was 41% among patients with a CR RAST of>200 units/ml, and 31% among patients with CR RAST 40–200 units/ml. This prevalence of reactivity was lower than that observed by plaque immunoassay (~60%) and may possibly be explained by increased sensitivity of the plaque assay, as compared to RIA. The $^{125}$I rBla g 4 showed strong reactivity with IgE ab (up to 45,000cpm bound, as compared to controls of <400 cpm), suggesting that the recombinant protein expressed the majority of B cell epitopes.

The biologic activity of rBla g 4 was assessed by quantitative intradermal skin testing of 7 selected CR allergic patients and 3 non-allergic controls. The results show that positive skin tests were obtained using $10^{-3}$–$10^{-5}$ $\mu$g/ml rBla g 4 and that skin test reactivity broadly correlated with serum IgE ab responses. In contrast, neither non-allergic controls, nor CR allergic patients with no detectable serum IgE ab to rBla g 4, gave positive skin tests using up to 1 $\mu$g/ml rBla g 4. These results showed that rBla g 4 was capable of inducing specific immediate hypersensitivity responses in CR allergic patients.

Homology Between Bla g 4 and Calycins

Sequence similarity searches showed that Bla g 4 was a member of the calycin family of proteins. Calycins are a diverse family of ~30 proteins, which include lipocalins and fatty acid binding proteins, whose function is to bind or transport small hydrophobic molecules. Examples include human retinol binding protein; butterfly bilin binding protein and tobacco hornworm insecticyanin (pigment binding protein). Calycins were not previously known to cause IgE responses, but sequence analyses unexpectedly revealed that this protein family also contained three major allergens: $\beta$-lactoglobulin from cows milk, and rodent urinary proteins (mouse urinary protein, MUP, and rat $\alpha_{2u}$-globulin). The overall homology between Bla g 4 and calycins was 18.9–23.9%, consistent with the low degree of sequence homology between other members of the family. Subsequent comparisons showed that the Bla g 4 sequence contained each of the three structurally conserved regions (SCR) of calycins proposed by Flower et al (29).

The molecular structures of bilin binding protein (BBP), insecticyanin, MUP and rat $\alpha_{2u}$-globulin had previously been determined at high resolution by X-ray crystallography. The characteristic calycin structure is a cup-shaped, eight strand, anti-parallel $\beta$-barrel, with a+1 topology (26–32). Structural models of Bla g 4 were constructed from the X-ray coordinates of butterfly BBP (which was selected as the base molecule because the positions of cysteine residues involved in disulphide bonds were conserved in the two proteins). Although the overall sequence identity between BBP and Bla g 4 is but 20%, it is comparable to that between BBP and the rodent urinary proteins, which have very similar conformations. The amino acid structures of Bla g 4, were substituted for those of BBP at positions where the two proteins differed. The positions of the mainchain and $\alpha$ atoms were retained for the substituted amino acids and the sidechains rebuilt. Loop regions, whose conformations could not be modeled directly from the BBP structure, were generated by conformational search calculations or loop searches. The model was minimized and equilibrated, followed by simulated annealing with a slow cool and a final minimization. Two models of Bla g 4 were generated. Both models fit the eight strand, anti-parallel $\beta$-barrel calycine structure, but differ primarily in the conformation of the large loop between the $\alpha$-helix and the C-terminal $\beta$ strand.

Expression of Bla g 4 in P. americana

Northern analysis was used to compare expression of mRNA encoding Bla g 4 in B. germanica and P. americana. An 0.75 kb B. germanica mRNA transcript hybridized with $^{32}$P-labelled Bla g 4 cDNA probe, but failed to hybridize to P. americana mRNA. Control experiments using a labelled N. crassa ribosomal DNA probe showed equivalent loading of mRNA from both CR species (FIG. 7A). To investigate the presence of genomic DNA encoding Bla g 4, PCR reactions on B germanica and P. americana genomic DNA were carried out using Bla g 4 specific primers and the PCR products were analyzed by probing Southern blots with $^{32}$p-labelled Bla g 4 cDNA. A predicted 523 bp DNA was amplified from the genomic DNA of both CR species and, in addition, a larger DNA (653 bp) was also detected (FIG. 7B). The two DNA's from both CR species hybridized to the Bla g 4 DNA probe. Taken together, these results suggest that B. germanica and P. americana have genomic DNA encoding Bla g 4; that the DNA is only transcribed into mRNA in B. germanica; and, consequently, that the Bla g 4 protein is only expressed in B. germanica.

DISCUSSION

Using molecular cloning techniques, we have identified and sequenced an important *B. germanica* allergen, Bla g 4, which binds IgE antibodies in 40–60% of CR allergic patients' sera. The recombinant allergen gave wheal and flare skin test responses at concentrations as low as $10^{-5}$ µg/ml. These results show unequivocally that Bla g 4 can elicit classical immediate hypersensitivity responses and the allergen would, therefore, be expected to contribute towards the symptoms of CR allergic patients. Bla g 4 is one of several CR allergens that we have cloned and sequenced, including Bla g 2 (an aspartic protease), Bla g 5 (a glutathione transferase), and Bla g 6 (troponin). Current evidence suggests that *B. germanica* produces at least five allergens that elicit IgE responses in 30–70% of CR allergic patients.

Although previous studies have shown allergenic cross-reactivity between *B. germanica* and *P. americana* extracts, only one of the allergens purified to date (Bla g 1 and its homologue, Per a 1) have been shown to cross-react. The nucleic acid hybridization studies reported here show that genomic DNA encoding Bla g 4 is present in *P. americana* (as well as in *B. germanica*), but that the *P. americana* DNA does not appear to be transcribed into Bla g 4 mRNA. On the basis of this evidence, it appears that Bla g 4 is produced by *B. germanica* and not by *P. americana*, and may be Blattella spp. specific, although its expression in a larger number of CR species remains to be tested. In the U.S., most patients are primarily exposed and sensitized to *B. germanica*, whereas in the Far East (e.g. Taiwan and Japan), *P. americana* and *P. fuliginosa* appear to be more important causes of sensitization. Our skin test and serum IgE antibody results with rBla g 4 suggest that the recombinant allergen will be useful for diagnosis of allergic reactions to *B. germanica* and raise the possibility that using a cocktail of allergens (including Bla g 2 and Bla g 5) it will be possible to use 3–4 recombinant proteins for both diagnostic (and therapeutic) purposes.

Recognition of Bla g 4 as a calycin (the first to be described in CR) provides insights into the biologic function of this protein. The homology with rodent urinary proteins, which are male pheromone transport proteins (32), raises the interesting possibility that Bla g 4 serves a similar function in CR. It is well known that *B. germanica* produces a variety of pheromones, including aggregation pheromones, excreted in the frass, and volatile sex pheromones, produced in glands located on the posterior abdominal tergites. There is also good evidence that CR allergens are secreted from CR bodies, or excreted in the feces, and there are anecdotal reports that CR can cause immediate skin reactions by crawling on the skin. Thus a plausible hypothesis is that Bla g 4 is a pheromone binding protein which is secreted along with male sex pheromones. The chemical structures of a number of CR pheromones have been defined and it will now be possible to investigate this hypothesis using photo-affinity labeling techniques and NMR to analyze pheromone binding to rBla g 4. If Bla g 4 could bind other calycin ligands, such as odorants or pigments, however, insect odorant binding proteins belong to different protein families and it is unlikely that odorant or pigment binding proteins would be secreted. If Bla g 4 is a pheromone binding protein, it could be a target for novel CR control strategies.

Our studies clearly show that calycins are a family of proteins that commonly cause IgE antibody responses. The calycin family contains several allergens associated with asthma (cockroach, rat, mouse and dog) as well as an allergen associated with food hypersensitivity (cow's milk β-lactoglobulin). Equine allergen has also been reported to belong to the calycin family. Whether calycins themselves have intrinsic properties that stimulate IgE production remains to be established. IgG and IgE antibody responses, and proliferative T cell responses, to rodent urinary proteins have been measured, and recent data shows IgE antibody binding to peptides from β-lactoglobulin. The availability of cloned Bla g 4 and other calycin sequences will enable these responses to be compared and the T cell epitopes involved in IgE responses to calycins to be defined. Since calycins have no enzymic activity, our results do not support the view that enzyme function per se is necessary to induce IgE responses, though enzymes could have adjuvant effects that enhance IgE production.

Rodent urinary proteins are the most abundant proteins secreted in the urine and become airborne on $7\mu$ particles in laboratory animal rooms (or houses containing rats). Inhalation of these particles, which stay airborne for several hours, causes IgE antibody responses, and can provoke acute asthma attacks. Similarly, when large CR populations develop in sub-standard housing, CR allergen accumulates at high levels in the dust and becomes airborne on $>10\mu$ particles following natural disturbance. The ability of antigen presenting cells and T cells to recognize this transient, low dose antigen exposure at mucosal surfaces to a large extent determines whether or not individuals will mount IgE antibody responses to environmental allergens. The present studies will make it possible to develop new immunotherapeutic strategies for CR allergy, including T cell based vaccines, and will also facilitate further analysis of the molecular events that mediate chronic inflammatory responses in CR allergic patients with asthma. One important step in their progress is the expression of recombinant allergens, discussed above.

PCR and Southern Analysis

*B. germanica* or *P. americans* genomic DNA was extracted from 0.1 g ground cockroach tissue using a Blood and Cell Culture DNA kit (QIAGEN, Chatsworth, Calif.). 100 ng CR genomic DNA was amplified by PCR using Taq polymerase (GeneAmp kit; Perkin-Elmer Cetus, Rockville, Md.). The following oligonucleotide primers, derived from the nucleotide sequence of Bla g 4 DNA, were used: 5' ACA GAT ACA TTG GCG GCG AA 3' (sense) and 5' GAC ATG TGG AGT GTA AG 3' (antisense), to amplify a 523 bp fragment (SEQ ID NO: 9,10). PCR products were electrophoresed in 1% agarose gel and DNA was transferred to nylon membrane. The Southern blot was hybridized with ($\alpha$-$^{32}$p] dCTP labeled 650 bp Bla g 4 cDNA probe at 37° C. and autoradiographed following 3 h exposure to Kodak XAR film.

Similar sequence homology comparisons were performed with the remaining allergens that are the subject of this invention. By comparing the sequences obtained with those of other sequences in various protein data bases, family association for the CR allergens characterized herein has been obtained. Thus, in addition to Bla g 2 being an aspartic protease, applicants have determined that Bla g 4 is a calycin, which family contains three other previously identified major allergens, β-lactoglobulin, rat urinary protein and mouse urinary protein. Macromolecular modeling techniques strongly suggest that calycins are a newly recognized family of proteins that induce IgE antibody responses by inhaled or oral routes and are associated with asthma and food sensitivity.

Similar studies demonstrate that Bla g 5 belongs to the family of glutathione transferases, and Bla g 6, to the family of troponins. This information makes it possible to interfere with the biologic function of these proteins, which provides a means of controlling CR infestation. Thus, interfering with the enzymatic activity of Bla g 2 and Bla g 5 provides one novel method of controlling CR infestation.

The purified and characterized allergens of this invention offer a variety of utilities. Each specific allergen, of course, can be used in conventional allergy testing (e.g., scratch testing) to identify, with specificity, the source of allergic reaction. This will allow more precise, more controlled response and intervention. Similarly, expression of recombinant allergens, with site or demain deletion or modification, may provide "allergic vaccines" for sensitive individuals. Intervention, both to suppress CR infestation, and asthmatic response, can be achieved using the subject matter of this invention.

The CR allergens of this invention have been described in terms of purification techniques, nucleotide sequence and amino acid sequence. Minor modifications of each remain within the scope of the claims, provided the modifications do not alter the biologic activity and allergenic nature of the isolated and characterized proteins. Such modifications remain within the scope of the claims presented below, unless specifically excluded by the recitations thereof.

( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 1317 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 3..1058

( x i ) SEQUENCE DESCRIPTION: SEQ ID NO:1:

```
AA  ATG  ATT  GGC  CTA  AAG  CTA  GTG  ACA  GTT  CTC  TTT  GCG  GTT  GCT  ACC           47
    Met  Ile  Gly  Leu  Lys  Leu  Val  Thr  Val  Leu  Phe  Ala  Val  Ala  Thr
    1              5                        10                       15

ATA  ACA  CAT  GCA  GCT  GAG  CTT  CAA  CGT  GTT  CCA  TTG  TAC  AAA  TTG  GTG          95
Ile  Thr  His  Ala  Ala  Glu  Leu  Gln  Arg  Val  Pro  Leu  Tyr  Lys  Leu  Val
                    20                        25                       30

CAC  GTT  TTC  ATT  AAC  ACT  CAA  TAC  GCT  GGT  ATA  ACC  AAG  ATT  GGA  AAC         143
His  Val  Phe  Ile  Asn  Thr  Gln  Tyr  Ala  Gly  Ile  Thr  Lys  Ile  Gly  Asn
               35                        40                       45

CAG  AAC  TTC  CTA  ACA  GTA  TTC  GAT  AGC  ACC  TCA  TGC  AAT  GTA  GTC  GTT         191
Gln  Asn  Phe  Leu  Thr  Val  Phe  Asp  Ser  Thr  Ser  Cys  Asn  Val  Val  Val
          50                        55                       60

GCC  AGT  CAA  GAA  TGC  GTT  GGT  GGA  GCT  TGT  GTA  TGT  CCA  AAT  CTA  CAA         239
Ala  Ser  Gln  Glu  Cys  Val  Gly  Gly  Ala  Cys  Val  Cys  Pro  Asn  Leu  Gln
     65                        70                       75

AAA  TAT  GAG  AAA  CTT  AAA  CCG  AAG  TAT  ATC  TCT  GAT  GGG  AAT  GTA  CAG         287
Lys  Tyr  Glu  Lys  Leu  Lys  Pro  Lys  Tyr  Ile  Ser  Asp  Gly  Asn  Val  Gln
80                        85                       90                       95

GTG  AAA  TTC  TTC  GAC  ACT  GGT  AGC  GCA  GTT  GGT  AGA  GGC  ATT  GAA  GAT         335
Val  Lys  Phe  Phe  Asp  Thr  Gly  Ser  Ala  Val  Gly  Arg  Gly  Ile  Glu  Asp
                    100                       105                      110

TCC  CTT  ACG  ATT  TCT  AAC  CTC  ACG  ACA  TCT  CAA  CAA  GAC  ATT  GTC  CTT         383
Ser  Leu  Thr  Ile  Ser  Asn  Leu  Thr  Thr  Ser  Gln  Gln  Asp  Ile  Val  Leu
               115                       120                      125

GCC  GAT  GAA  CTC  AGT  CAA  GAA  GTC  TGC  ATT  CTA  TCT  GCT  GAC  GTA  GTT         431
Ala  Asp  Glu  Leu  Ser  Gln  Glu  Val  Cys  Ile  Leu  Ser  Ala  Asp  Val  Val
          130                       135                      140

GTA  GGA  ATA  GCA  GCC  CCA  GGA  TGC  CCT  AAT  GCA  CTG  AAA  GGA  AAA  ACT         479
Val  Gly  Ile  Ala  Ala  Pro  Gly  Cys  Pro  Asn  Ala  Leu  Lys  Gly  Lys  Thr
     145                       150                      155
```

```
GTT CTC GAA AAC TTT GTC GAA GAA AAT CTT ATT GCG CCT GTC TTT TCT        527
Val Leu Glu Asn Phe Val Glu Glu Asn Leu Ile Ala Pro Val Phe Ser
160                 165                 170                 175

ATT CAT CAT GCT AGA TTT CAA GAT GGA GAA CAT TTC GGA GAA ATT ATT        575
Ile His His Ala Arg Phe Gln Asp Gly Glu His Phe Gly Glu Ile Ile
                180                 185                 190

TTC GGA GGT TCT GAT TGG AAA TAC GTT GAT GGT GAA TTC ACT TAT GTT        623
Phe Gly Gly Ser Asp Trp Lys Tyr Val Asp Gly Glu Phe Thr Tyr Val
            195                 200                 205

CCA CTT GTG GGT GAT GAT TCC TGG AAG TTC AGG CTG GAT GGT GTG AAA        671
Pro Leu Val Gly Asp Asp Ser Trp Lys Phe Arg Leu Asp Gly Val Lys
        210                 215                 220

ATA GGT GAC ACA ACT GTT GCT CCA GCA GGT ACA CAG GCC ATC ATC GAC        719
Ile Gly Asp Thr Thr Val Ala Pro Ala Gly Thr Gln Ala Ile Ile Asp
    225                 230                 235

ACA AGC AAA GCT ATC ATT GTC GGA CCT AAA GCC TAT GTT AAT CCA ATC        767
Thr Ser Lys Ala Ile Ile Val Gly Pro Lys Ala Tyr Val Asn Pro Ile
240                 245                 250                 255

AAC GAA GCT ATT GGG TGT GTA GTG GAA AAG ACA ACA ACC AGG AGA ATA        815
Asn Glu Ala Ile Gly Cys Val Val Glu Lys Thr Thr Thr Arg Arg Ile
                260                 265                 270

TGC AAG CTT GAC TGC AGC AAG ATA CCA TCT CTC CCT GAT GTC ACA TTT        863
Cys Lys Leu Asp Cys Ser Lys Ile Pro Ser Leu Pro Asp Val Thr Phe
            275                 280                 285

GTG ATC AAT GGC AGG AAT TTC AAC ATC AGC TCA CAA TAT TAC ATC CAA        911
Val Ile Asn Gly Arg Asn Phe Asn Ile Ser Ser Gln Tyr Tyr Ile Gln
        290                 295                 300

CAG AAC GGG AAC TTG TGC TAT TCC GGC TTC CAA CCA TGC GGT CAC TCC        959
Gln Asn Gly Asn Leu Cys Tyr Ser Gly Phe Gln Pro Cys Gly His Ser
    305                 310                 315

GAT CAC TTT TTT ATT GGT GAC TTC TTT GTT GAT CAT TAT TAT TCT GAA       1007
Asp His Phe Phe Ile Gly Asp Phe Phe Val Asp His Tyr Tyr Ser Glu
320                 325                 330                 335

TTC AAC TGG GAG AAC AAG ACC ATG GGA TTC GGC CGT TCA GTA GAA AGC       1055
Phe Asn Trp Glu Asn Lys Thr Met Gly Phe Gly Arg Ser Val Glu Ser
                340                 345                 350

GTC TAAGAATTTC AACATCAAGA TGGACTTCAG AGATTACTTC GGAATCACTA            1108
Val

ATAAGACATT CACGAGACTT ACGAAGACCA CTACAGTTTT GGATATGAAT GATGACAAAT     1168

AACTGAAGAC TTTTCATTAT ATGACATGGA GAAGATTTTT TTAAAGTCGC CTATTATTAC     1228

TTTTTTCGCA CACTTTTATG TATACAGCTA CTGATGTCTT AAAATAAACT GGAAATATTT     1288

TGAATTTTCT AAAAAAAAAA AAAAAAAA                                        1317
```

( 2 ) INFORMATION FOR SEQ ID NO:2:

( i ) SEQUENCE CHARACTERISTICS:
        ( A ) LENGTH: 352 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ile Gly Leu Lys Leu Val Thr Val Leu Phe Ala Val Ala Thr Ile
1               5                   10                  15

Thr His Ala Ala Glu Leu Gln Arg Val Pro Leu Tyr Lys Leu Val His
                20                  25                  30

Val Phe Ile Asn Thr Gln Tyr Ala Gly Ile Thr Lys Ile Gly Asn Gln
            35                  40                  45
```

|     |     |     |     |     |     |     |     |     |     |     |     |     |     |
|---|---|---|---|---|---|---|---|---|---|---|---|---|---|
| Asn | Phe | Leu | Thr | Val | Phe | Asp | Ser | Thr | Ser | Cys | Asn | Val | Val | Ala |
|     | 50  |     |     |     |     | 55  |     |     |     | 60  |     |     |     |
| Ser | Gln | Glu | Cys | Val | Gly | Gly | Ala | Cys | Val | Cys | Pro | Asn | Leu | Gln | Lys |
| 65  |     |     |     |     | 70  |     |     |     | 75  |     |     |     |     | 80  |
| Tyr | Glu | Lys | Leu | Lys | Pro | Lys | Tyr | Ile | Ser | Asp | Gly | Asn | Val | Gln | Val |
|     |     |     |     | 85  |     |     |     |     | 90  |     |     |     |     | 95  |
| Lys | Phe | Phe | Asp | Thr | Gly | Ser | Ala | Val | Gly | Arg | Gly | Ile | Glu | Asp | Ser |
|     |     |     | 100 |     |     |     |     | 105 |     |     |     |     | 110 |     |
| Leu | Thr | Ile | Ser | Asn | Leu | Thr | Thr | Ser | Gln | Gln | Asp | Ile | Val | Leu | Ala |
|     |     | 115 |     |     |     |     | 120 |     |     |     |     | 125 |     |     |     |
| Asp | Glu | Leu | Ser | Gln | Glu | Val | Cys | Ile | Leu | Ser | Ala | Asp | Val | Val | Val |
|     | 130 |     |     |     |     | 135 |     |     |     |     | 140 |     |     |     |     |
| Gly | Ile | Ala | Ala | Pro | Gly | Cys | Pro | Asn | Ala | Leu | Lys | Gly | Lys | Thr | Val |
| 145 |     |     |     |     | 150 |     |     |     |     | 155 |     |     |     |     | 160 |
| Leu | Glu | Asn | Phe | Val | Glu | Glu | Asn | Leu | Ile | Ala | Pro | Val | Phe | Ser | Ile |
|     |     |     |     | 165 |     |     |     |     | 170 |     |     |     |     | 175 |     |
| His | His | Ala | Arg | Phe | Gln | Asp | Gly | Glu | His | Phe | Gly | Glu | Ile | Ile | Phe |
|     |     |     | 180 |     |     |     |     | 185 |     |     |     |     | 190 |     |     |
| Gly | Gly | Ser | Asp | Trp | Lys | Tyr | Val | Asp | Gly | Glu | Phe | Thr | Tyr | Val | Pro |
|     |     | 195 |     |     |     |     | 200 |     |     |     |     | 205 |     |     |     |
| Leu | Val | Gly | Asp | Asp | Ser | Trp | Lys | Phe | Arg | Leu | Asp | Gly | Val | Lys | Ile |
|     | 210 |     |     |     |     | 215 |     |     |     |     | 220 |     |     |     |     |
| Gly | Asp | Thr | Thr | Val | Ala | Pro | Ala | Gly | Thr | Gln | Ala | Ile | Ile | Asp | Thr |
| 225 |     |     |     |     | 230 |     |     |     |     | 235 |     |     |     |     | 240 |
| Ser | Lys | Ala | Ile | Ile | Val | Gly | Pro | Lys | Ala | Tyr | Val | Asn | Pro | Ile | Asn |
|     |     |     |     | 245 |     |     |     |     | 250 |     |     |     |     | 255 |     |
| Glu | Ala | Ile | Gly | Cys | Val | Val | Glu | Lys | Thr | Thr | Thr | Arg | Arg | Ile | Cys |
|     |     |     | 260 |     |     |     |     | 265 |     |     |     |     | 270 |     |     |
| Lys | Leu | Asp | Cys | Ser | Lys | Ile | Pro | Ser | Leu | Pro | Asp | Val | Thr | Phe | Val |
|     |     | 275 |     |     |     |     | 280 |     |     |     |     | 285 |     |     |     |
| Ile | Asn | Gly | Arg | Asn | Phe | Asn | Ile | Ser | Ser | Gln | Tyr | Tyr | Ile | Gln | Gln |
|     | 290 |     |     |     |     | 295 |     |     |     |     | 300 |     |     |     |     |
| Asn | Gly | Asn | Leu | Cys | Tyr | Ser | Gly | Phe | Gln | Pro | Cys | Gly | His | Ser | Asp |
| 305 |     |     |     |     | 310 |     |     |     |     | 315 |     |     |     |     | 320 |
| His | Phe | Phe | Ile | Gly | Asp | Phe | Phe | Val | Asp | His | Tyr | Tyr | Ser | Glu | Phe |
|     |     |     |     | 325 |     |     |     |     | 330 |     |     |     |     | 335 |     |
| Asn | Trp | Glu | Asn | Lys | Thr | Met | Gly | Phe | Gly | Arg | Ser | Val | Glu | Ser | Val |
|     |     |     | 340 |     |     |     |     | 345 |     |     |     |     | 350 |     |     |

( 2 ) INFORMATION FOR SEQ ID NO:3:

( i ) SEQUENCE CHARACTERISTICS:
        ( A ) LENGTH: 629 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 2..547

( x i ) SEQUENCE DESCRIPTION: SEQ ID NO:3:

| C | GCA | GTT | TTG | GCA | CTA | TGT | GCA | ACA | GAT | ACA | TTG | GCG | AAC | GAA | GAT | 46 |
|---|---|---|---|---|---|---|---|---|---|---|---|---|---|---|---|---|
|   | Ala | Val | Leu | Ala | Leu | Cys | Ala | Thr | Asp | Thr | Leu | Ala | Asn | Glu | Asp |   |
|   | 355 |     |     |     |     | 360 |     |     |     |     | 365 |     |     |     |     |   |

-continued

```
TGT TTT AGA CAT GAA TCA TTG GTT CCA AAC CTT GAT TAT GAA AGG TTC      94
Cys Phe Arg His Glu Ser Leu Val Pro Asn Leu Asp Tyr Glu Arg Phe
        370             375             380

AGA GGT TCG TGG ATT ATT GCA GCC GGC ACT TCC GAA GCG CTC ACC CAA     142
Arg Gly Ser Trp Ile Ile Ala Ala Gly Thr Ser Glu Ala Leu Thr Gln
385             390             395

TAC AAA TGC TGG ATC GAC AGG TTT TCA TAT GAC GAT GCG TTG GTT TCT     190
Tyr Lys Cys Trp Ile Asp Arg Phe Ser Tyr Asp Asp Ala Leu Val Ser
400             405             410             415

AAG TAT ACT GAT TCA CAA GGA AAG AAT AGG ACT ACT ATC AGA GGA CGA     238
Lys Tyr Thr Asp Ser Gln Gly Lys Asn Arg Thr Thr Ile Arg Gly Arg
            420             425             430

ACT AAA TTT GAA GGC AAC AAG TTT ACT ATC GAT TAT AAT GAT AAA GGG     286
Thr Lys Phe Glu Gly Asn Lys Phe Thr Ile Asp Tyr Asn Asp Lys Gly
        435             440             445

AAA GCA TTT TCT GCG CCA TAC TCT GTT CTA GCA ACT GAT TAC GAA AAT     334
Lys Ala Phe Ser Ala Pro Tyr Ser Val Leu Ala Thr Asp Tyr Glu Asn
        450             455             460

TAC GCA ATT GTG GAA GGC TGT CCC GCT GCA GCT AAT GGA CAT GTA ATT     382
Tyr Ala Ile Val Glu Gly Cys Pro Ala Ala Ala Asn Gly His Val Ile
465             470             475

TAT GTT CAA ATC CGA TTT TCG GTG AGG AGA TTT CAC CCC AAG CTG GGT     430
Tyr Val Gln Ile Arg Phe Ser Val Arg Arg Phe His Pro Lys Leu Gly
480             485             490             495

GAT AAA GAA ATG ATA CAG CAC TAC ACT TTG GAT CAG GTG AAT CAA CAC     478
Asp Lys Glu Met Ile Gln His Tyr Thr Leu Asp Gln Val Asn Gln His
            500             505             510

AAG AAG GCT ATA GAA GAA GAC TTA AAG CAC TTC AAT TTG AAG TAC GAG     526
Lys Lys Ala Ile Glu Glu Asp Leu Lys His Phe Asn Leu Lys Tyr Glu
        515             520             525

GAC TTA CAC TCC ACA TGT CAC TAAGTATGAA ATGTTCATAT TTATTGTAGG        577
Asp Leu His Ser Thr Cys His
        530

AAAATAAAAC CTTCTAATGA ATTAAAAAAA AAAAAAAAAA AAAAAAAAAA AA           629
```

( 2 ) INFORMATION FOR SEQ ID NO:4:

( i ) SEQUENCE CHARACTERISTICS:
        ( A ) LENGTH: 182 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Ala Val Leu Ala Leu Cys Ala Thr Asp Thr Leu Ala Asn Glu Asp Cys
1               5               10              15

Phe Arg His Glu Ser Leu Val Pro Asn Leu Asp Tyr Glu Arg Phe Arg
            20              25              30

Gly Ser Trp Ile Ile Ala Ala Gly Thr Ser Glu Ala Leu Thr Gln Tyr
        35              40              45

Lys Cys Trp Ile Asp Arg Phe Ser Tyr Asp Asp Ala Leu Val Ser Lys
    50              55              60

Tyr Thr Asp Ser Gln Gly Lys Asn Arg Thr Thr Ile Arg Gly Arg Thr
65              70              75              80

Lys Phe Glu Gly Asn Lys Phe Thr Ile Asp Tyr Asn Asp Lys Gly Lys
            85              90              95

Ala Phe Ser Ala Pro Tyr Ser Val Leu Ala Thr Asp Tyr Glu Asn Tyr
            100             105             110
```

```
Ala  Ile  Val  Glu  Gly  Cys  Pro  Ala  Ala  Ala  Asn  Gly  His  Val  Ile  Tyr
          115                      120                     125

Val  Gln  Ile  Arg  Phe  Ser  Val  Arg  Arg  Phe  His  Pro  Lys  Leu  Gly  Asp
          130                      135                     140

Lys  Glu  Met  Ile  Gln  His  Tyr  Thr  Leu  Asp  Gln  Val  Asn  Gln  His  Lys
145                           150                     155                     160

Lys  Ala  Ile  Glu  Glu  Asp  Leu  Lys  His  Phe  Asn  Leu  Lys  Tyr  Glu  Asp
               165                           170                     175

Leu  His  Ser  Thr  Cys  His
               180
```

(2) INFORMATION FOR SEQ ID NO:5:

(i) SEQUENCE CHARACTERISTICS:
        (A) LENGTH: 1140 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 3..602

(xi) SEQUENCE DESCRIPTION: SEQ ID NO:5:

```
CT   TAT  AAA  CTG  ACA  TAC  TGT  CCC  GTG  AAG  GCT  CTG  GGA  GAG  CCA  ATT    47
     Tyr  Lys  Leu  Thr  Tyr  Cys  Pro  Val  Lys  Ala  Leu  Gly  Glu  Pro  Ile
               185                      190                     195

CGC  TTC  CTT  CTG  TCT  TAT  GGA  GAG  AAA  GAT  TTT  GAA  GAT  TAT  CGT  TTC    95
Arg  Phe  Leu  Leu  Ser  Tyr  Gly  Glu  Lys  Asp  Phe  Glu  Asp  Tyr  Arg  Phe
               200                      205                     210

CAG  GAG  GGA  GAT  TGG  CCT  AAT  TTG  AAA  CCT  TCC  ATG  CCA  TTT  GGT  AAA   143
Gln  Glu  Gly  Asp  Trp  Pro  Asn  Leu  Lys  Pro  Ser  Met  Pro  Phe  Gly  Lys
          215                      220                     225

ACA  CCA  GTG  TTG  GAG  ATT  GAT  GGG  AAG  CAA  ACA  CAC  CAG  TCT  GTT  GCC   191
Thr  Pro  Val  Leu  Glu  Ile  Asp  Gly  Lys  Gln  Thr  His  Gln  Ser  Val  Ala
230                           235                     240                     245

ATT  TCT  CGC  TAT  CTT  GGT  AAG  CAG  TTT  GGC  CTC  AGT  GGT  AAG  GAT  GAT   239
Ile  Ser  Arg  Tyr  Leu  Gly  Lys  Gln  Phe  Gly  Leu  Ser  Gly  Lys  Asp  Asp
                    250                      255                     260

TGG  GAG  AAC  TTG  GAG  ATC  GAC  ATG  ATC  GTC  GAC  ACC  ATC  TCT  GAC  TTC   287
Trp  Glu  Asn  Leu  Glu  Ile  Asp  Met  Ile  Val  Asp  Thr  Ile  Ser  Asp  Phe
               265                      270                     275

AGG  GCT  GCC  ATT  GCT  AAT  TAC  CAT  TAT  GAT  GCT  GAT  GAA  AAT  TCA  AAG   335
Arg  Ala  Ala  Ile  Ala  Asn  Tyr  His  Tyr  Asp  Ala  Asp  Glu  Asn  Ser  Lys
          280                      285                     290

CAG  AAG  AAA  TGG  GAC  CCT  CTC  AAG  AAG  GAA  ACC  ATT  CCT  TAC  TAC  ACC   383
Gln  Lys  Lys  Trp  Asp  Pro  Leu  Lys  Lys  Glu  Thr  Ile  Pro  Tyr  Tyr  Thr
     295                      300                     305

AAA  AAG  TTT  GAT  GAA  GTG  GTG  AAG  GCT  AAC  GGA  GGA  TAC  CTT  GCT  GCT   431
Lys  Lys  Phe  Asp  Glu  Val  Val  Lys  Ala  Asn  Gly  Gly  Tyr  Leu  Ala  Ala
310                           315                     320                     325

GGA  AAG  CTG  ACA  TGG  GCA  GAC  TTC  TAC  TTC  GTT  GCC  ATT  CTC  GAC  TAT   479
Gly  Lys  Leu  Thr  Trp  Ala  Asp  Phe  Tyr  Phe  Val  Ala  Ile  Leu  Asp  Tyr
                    330                      335                     340

TTG  AAT  CAC  ATG  GCT  AAA  GAA  GAC  CTG  GTG  GCC  AAT  CAA  CCC  AAT  TTG   527
Leu  Asn  His  Met  Ala  Lys  Glu  Asp  Leu  Val  Ala  Asn  Gln  Pro  Asn  Leu
               345                      350                     355

AAG  GCT  TTG  CGG  GAG  AAA  GTA  TTG  GGT  TTG  CCT  GCT  ATC  AAA  GCA  TGG   575
Lys  Ala  Leu  Arg  Glu  Lys  Val  Leu  Gly  Leu  Pro  Ala  Ile  Lys  Ala  Trp
          360                      365                     370
```

```
GTC  GCC  AAG  CGT  CCT  CCT  ACA  GAT  CTG  TAAGAAAAAT GTGCCATGGC              622
Val  Ala  Lys  Arg  Pro  Pro  Thr  Asp  Leu
          375                      380

AAAAAAATTC ATGTTGCATG TAACACTGAG ATCATAACGA TGTTCTAAAA GAAATTTTGT               682

TACGCATAAT GATTTTATGA AAGTATTTTG TTAGCAGCTT TGCTCTATAA TAATCACTAG              742

ACCATATTTA AAAGGCAAAA ACGAACATTT TCTTCATAAA AGGCAAAAAT AGCCAAAAAA              802

TACTTTTGTA TTAAAATATT CATTGACGCT GATTCTTACA TTTAATTCTT CACAATTTAA              862

GAATTTTTTA ACAATAGTAA TTACGATCAA CATTTCAGAT CTGTTTAGAT ATGATTGCAA              922

AGCTTGTTTA TAATCAGAAA ATGACTTCCT AAAATCAACA GCATATGGCG CAAAATTTTT              982

CGTTCTAAAT TTCCAGTTTT TTAAATGTAT AATTTTTTG GTAAACTTTT ATTTACTAGA              1042

AATTTGATCC AGAAGTAGAC TGATAATTTC CTTACTTAC TTTTGGTAT TAAACAAAGT              1102

TGGAAACAAA ATAATTTTGA AAAAAAAAAA AAAAAAA                                      1140
```

( 2 ) INFORMATION FOR SEQ ID NO:6:

( i ) SEQUENCE CHARACTERISTICS:
( A ) LENGTH: 200 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Tyr  Lys  Leu  Thr  Tyr  Cys  Pro  Val  Lys  Ala  Leu  Gly  Glu  Pro  Ile  Arg
  1                 5                      10                      15

Phe  Leu  Leu  Ser  Tyr  Gly  Glu  Lys  Asp  Phe  Glu  Asp  Tyr  Arg  Phe  Gln
               20                      25                      30

Glu  Gly  Asp  Trp  Pro  Asn  Leu  Lys  Pro  Ser  Met  Pro  Phe  Gly  Lys  Thr
          35                      40                      45

Pro  Val  Leu  Glu  Ile  Asp  Gly  Lys  Gln  Thr  His  Gln  Ser  Val  Ala  Ile
     50                      55                      60

Ser  Arg  Tyr  Leu  Gly  Lys  Gln  Phe  Gly  Leu  Ser  Gly  Lys  Asp  Asp  Trp
 65                      70                      75                      80

Glu  Asn  Leu  Glu  Ile  Asp  Met  Ile  Val  Asp  Thr  Ile  Ser  Asp  Phe  Arg
                85                      90                      95

Ala  Ala  Ile  Ala  Asn  Tyr  His  Tyr  Asp  Ala  Asp  Glu  Asn  Ser  Lys  Gln
               100                     105                     110

Lys  Lys  Trp  Asp  Pro  Leu  Lys  Lys  Glu  Thr  Ile  Pro  Tyr  Tyr  Thr  Lys
          115                     120                     125

Lys  Phe  Asp  Glu  Val  Val  Lys  Ala  Asn  Gly  Gly  Tyr  Leu  Ala  Ala  Gly
     130                     135                     140

Lys  Leu  Thr  Trp  Ala  Asp  Phe  Tyr  Phe  Val  Ala  Ile  Leu  Asp  Tyr  Leu
145                     150                     155                     160

Asn  His  Met  Ala  Lys  Glu  Asp  Leu  Val  Ala  Asn  Gln  Pro  Asn  Leu  Lys
               165                     170                     175

Ala  Leu  Arg  Glu  Lys  Val  Leu  Gly  Leu  Pro  Ala  Ile  Lys  Ala  Trp  Val
          180                     185                     190

Ala  Lys  Arg  Pro  Pro  Thr  Asp  Leu
     195                     200
```

( 2 ) INFORMATION FOR SEQ ID NO:7:

( i ) SEQUENCE CHARACTERISTICS:
( A ) LENGTH: 836 base pairs
( B ) TYPE: nucleic acid
( C ) STRANDEDNESS: double (D) TOPOLOGY: linear (ii) MOLECULE TYPE: DNA (genomic)

(ix) FEATURE:
    (A) NAME/KEY: CDS
    (B) LOCATION: 3..491

(xi) SEQUENCE DESCRIPTION: SEQ ID NO:7:

| GA | GAG | GTA | CCA | CAA | GCC | ACC | ACC | AAC | AAC | ACC | GTC | GCC | ATG | GAT | GAA | 47 |
|---|---|---|---|---|---|---|---|---|---|---|---|---|---|---|---|---|
| | Glu | Val | Pro | Gln | Ala | Thr | Thr | Asn | Asn | Thr | Val | Ala | Met | Asp | Glu | |
| | | | | 205 | | | | | 210 | | | | | | 215 | |

| ATT | CCA | GCA | GAA | CAG | GTC | GTA | CTG | TTG | AAG | AAG | GCT | TTC | GAT | GCC | TTC | 95 |
|---|---|---|---|---|---|---|---|---|---|---|---|---|---|---|---|---|
| Ile | Pro | Ala | Glu | Gln | Val | Val | Leu | Leu | Lys | Lys | Ala | Phe | Asp | Ala | Phe | |
| 220 | | | | | | | | | 225 | | | | | | 230 | |

| GAT | CGT | GAG | AAG | AAG | GGT | TGC | ATC | TCC | ACT | GAG | ATG | GTA | GGC | ACC | ATC | 143 |
|---|---|---|---|---|---|---|---|---|---|---|---|---|---|---|---|---|
| Asp | Arg | Glu | Lys | Lys | Gly | Cys | Ile | Ser | Thr | Glu | Met | Val | Gly | Thr | Ile | |
| | | 235 | | | | | | | 240 | | | | | 245 | | |

| CTG | GAG | ATG | TTG | GGT | ACC | CGT | CTG | GAC | CAG | GAC | ATG | CTG | GAT | GAG | ATC | 191 |
|---|---|---|---|---|---|---|---|---|---|---|---|---|---|---|---|---|
| Leu | Glu | Met | Leu | Gly | Thr | Arg | Leu | Asp | Gln | Asp | Met | Leu | Asp | Glu | Ile | |
| | | 250 | | | | | 255 | | | | | 260 | | | | |

| ATC | GCT | GAA | GTC | GAC | GCT | GAC | GGT | TCC | GGT | GAG | CTG | GAG | TTC | GAG | GAA | 239 |
|---|---|---|---|---|---|---|---|---|---|---|---|---|---|---|---|---|
| Ile | Ala | Glu | Val | Asp | Ala | Asp | Gly | Ser | Gly | Glu | Leu | Glu | Phe | Glu | Glu | |
| | 265 | | | | | 270 | | | | | 275 | | | | | |

| TTC | TGT | ACA | TTG | GCC | TCT | AGG | TTC | CTG | GTT | GAA | GAG | GAT | CGT | GAA | GCC | 287 |
|---|---|---|---|---|---|---|---|---|---|---|---|---|---|---|---|---|
| Phe | Cys | Thr | Leu | Ala | Ser | Arg | Phe | Leu | Val | Glu | Glu | Asp | Arg | Glu | Ala | |
| 280 | | | | | 285 | | | | | 290 | | | | | 295 | |

| ATG | CAG | CAC | GAA | CTC | CGA | GAA | GCT | TTC | AGA | TTA | TAC | GAC | AAG | GAA | GGC | 335 |
|---|---|---|---|---|---|---|---|---|---|---|---|---|---|---|---|---|
| Met | Gln | His | Glu | Leu | Arg | Glu | Ala | Phe | Arg | Leu | Tyr | Asp | Lys | Glu | Gly | |
| | | | | 300 | | | | | 305 | | | | | 310 | | |

| AAC | GGC | TAC | ATC | ACA | ACA | GCT | GTC | CTA | CGC | GAG | ATC | CTG | AAG | GAG | CTC | 383 |
|---|---|---|---|---|---|---|---|---|---|---|---|---|---|---|---|---|
| Asn | Gly | Tyr | Ile | Thr | Thr | Ala | Val | Leu | Arg | Glu | Ile | Leu | Lys | Glu | Leu | |
| | | | 315 | | | | | 320 | | | | | 325 | | | |

| GAT | GAC | AAA | ATA | ACC | GCT | GAG | GAC | TTG | GAT | ATG | ATG | ATT | GAG | GAA | ATT | 431 |
|---|---|---|---|---|---|---|---|---|---|---|---|---|---|---|---|---|
| Asp | Asp | Lys | Ile | Thr | Ala | Glu | Asp | Leu | Asp | Met | Met | Ile | Glu | Glu | Ile | |
| | | 330 | | | | | 335 | | | | | 340 | | | | |

| GAC | TCT | GAC | GGT | TCC | GGA | ACC | GTT | GAC | TTT | GAT | GAA | TTC | ATG | GAA | GTC | 479 |
|---|---|---|---|---|---|---|---|---|---|---|---|---|---|---|---|---|
| Asp | Ser | Asp | Gly | Ser | Gly | Thr | Val | Asp | Phe | Asp | Glu | Phe | Met | Glu | Val | |
| | 345 | | | | | 350 | | | | | 355 | | | | | |

| ATG | ACT | GGA | GAA | TAAATGCCAT | TTTATGCTTC | AAAACTTAAG | TCATCTTTCT | 531 |
|---|---|---|---|---|---|---|---|---|
| Met | Thr | Gly | Glu | | | | | |
| 360 | | | | | | | | |

TCAATGGACT GCCTCCGAGC TATCTGAGCT TTAGGAATGA GTTCATCCAA AAGACAATCT    591

TGTATTCTTA TAATCGTATG GCAATGTAAA TTATCATTCA ACATCATTTT GATAAATTGT    651

TACTAAATTT TATGTTTCTG TACATATCAA ATTTTATTAT GAAATTTATT GGGGCCTGCC    711

TATAAACAAG ACAATGTGTA TATGTTTACT TTAACACCAG TATTATTATA CAATAATGTG    771

AAATAAAAGA CTTCAGAACT TTGTATGAAA AAAAAAAAA AAAAAAAAA AAAAAAAAA      831

AAAAA                                                                836

(2) INFORMATION FOR SEQ ID NO:8:

(i) SEQUENCE CHARACTERISTICS:
        (A) LENGTH: 163 amino acids
        (B) TYPE: amino acid
        (D) TOPOLOGY: linear (ii) MOLECULE TYPE: protein (xi) SEQUENCE DESCRIPTION: SEQ ID NO:8:

| Glu | Val | Pro | Gln | Ala | Thr | Thr | Asn | Asn | Thr | Val | Ala | Met | Asp | Glu | Ile |
|---|---|---|---|---|---|---|---|---|---|---|---|---|---|---|---|
| 1 | | | | 5 | | | | | 10 | | | | | 15 | |

-continued

```
Pro  Ala  Glu  Gln  Val  Val  Leu  Leu  Lys  Lys  Ala  Phe  Asp  Ala  Phe  Asp
               20                      25                      30
Arg  Glu  Lys  Lys  Gly  Cys  Ile  Ser  Thr  Glu  Met  Val  Gly  Thr  Ile  Leu
          35                 40                           45
Glu  Met  Leu  Gly  Thr  Arg  Leu  Asp  Gln  Asp  Met  Leu  Asp  Glu  Ile  Ile
     50                      55                      60
Ala  Glu  Val  Asp  Ala  Asp  Gly  Ser  Gly  Glu  Leu  Glu  Phe  Glu  Glu  Phe
65                       70                      75                           80
Cys  Thr  Leu  Ala  Ser  Arg  Phe  Leu  Val  Glu  Glu  Asp  Arg  Glu  Ala  Met
                    85                 90                           95
Gln  His  Glu  Leu  Arg  Glu  Ala  Phe  Arg  Leu  Tyr  Asp  Lys  Glu  Gly  Asn
               100                    105                     110
Gly  Tyr  Ile  Thr  Thr  Ala  Val  Leu  Arg  Glu  Ile  Leu  Lys  Glu  Leu  Asp
          115                      120                125
Asp  Lys  Ile  Thr  Ala  Glu  Asp  Leu  Asp  Met  Met  Ile  Glu  Glu  Ile  Asp
     130                     135                     140
Ser  Asp  Gly  Ser  Gly  Thr  Val  Asp  Phe  Asp  Glu  Phe  Met  Glu  Val  Met
145                     150                     155                          160
Thr  Gly  Glu
```

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide primer"

( x i ) SEQUENCE DESCRIPTION: SEQ ID NO:9:

ACAGATACAT TGGCGGCGAA    20

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide primer"

( x i ) SEQUENCE DESCRIPTION: SEQ ID NO:10:

GACATGTGGA GTGTAAG    17

What is claimed is:

1. A purified cockroach (CR) allergen selected from the group consisting of Bla g 4, Bla g 5 and Bla g 6.

2. An isolated nucleotide sequence which encodes a CR antigen selected from the group consisting of Bla g 4, Bla g 5 and Bla g 6.

3. An isolated CR allergen comprising the amino acid sequence of Bla g 4, Bla g 5 or Bla g 6, as shown in FIGS. 2, 3 and 4, respectively (SEQ ID NO: 4,6,8).

4. A recombinantly expressed CR allergen, selected from the group consisting of Bla g 4, Bla g 5 and Bla g 6.

5. An isolated nucleotide sequence that encodes Bla g 2 having the amino acid sequence shown in FIG. 1 (SEQ ID NO: 2).

6. An expression vector comprising the nucleotide sequence of claim 2 that encodes the Bla g 4 CR antigen.

7. An expression vector comprising the nucleotide sequence of claim 2 that encodes the Bla g 5 CR antigen.

8. An expression vector comprising the nucleotide sequence of claim 2 that encodes the Bla g 6 CR antigen.

9. A host cell comprising the expression vector of claim 6.

10. A host cell comprising the expression vector of claim 7.

11. A host cell comprising the expression vector of claim 8.

12. A method of producing Bla g 4 CR antigen comprising culturing the host cell of claim 9 under conditions such that said nucleotide sequence is expressed and said Bla g 4 CR antigen is thereby produced, and isolating said Bla g 4 antigen.

13. A method of producing Bla g 5 CR antigen comprising culturing the host cell of claim 10 under conditions such that said nucleotide sequence is expressed and said Bla g 5 CR antigen is thereby produced, and isolating said Bla g 5 antigen.

14. A method of producing Bla g 6 CR antigen comprising culturing the host cell of claim 11 under conditions such that said nucleotide sequence is expressed and said Bla g 6 CR antigen is thereby produced, and isolating said Bla g 6 antigen.

15. An expression vector comprising the nucleotide sequence of claim 5 that encodes the Bla g 2 CR antigen.

16. A host cell comprising the expression vector of claim 15.

17. A method of producing Bla g 2 CR antigen comprising culturing the host cell of claim 16 under conditions such that said nucleotide sequence is expressed and said Bla g 2 CR antigen is thereby produced, and isolating said Bla g 2 antigen.

\* \* \* \* \*